United States Patent [19]
Koshishiba et al.

[11] Patent Number: 5,351,278
[45] Date of Patent: Sep. 27, 1994

[54] X-RAY TOMOGRAPHY METHOD AND APPARATUS THEREOF

[75] Inventors: Hiroya Koshishiba, Yokohama; Mihoko Yoshimura, Kamakura, both of Japan

[73] Assignee: Hitachi, Ltd., Tokyo, Japan

[21] Appl. No.: 29,041

[22] Filed: Mar. 9, 1993

[30] Foreign Application Priority Data

Mar. 9, 1992 [JP] Japan .................................. 4-050788
Jun. 17, 1992 [JP] Japan .................................. 4-158121

[51] Int. Cl.$^5$ ........................................... G01N 23/00
[52] U.S. Cl. ......................................... 378/22; 378/24
[58] Field of Search ..................................... 378/24, 22

[56] References Cited

U.S. PATENT DOCUMENTS 2,998,518 8/1961 Guntert ................................. 378/22

OTHER PUBLICATIONS

"Spatial Filtering to Improve Transverse Tomography" Peters, IEEE Transactions on Biomedical Engineering, vol. 21, No. 3, May 1974 pp. 214–219.

Primary Examiner—Graig E. Church
Attorney, Agent, or Firm—Antonelli, Terry Stout & Kraus

[57] ABSTRACT

This invention relates to an X-ray tomography apparatus and a method therefor. The apparatus comprises an X-ray source for irradiating X rays to an inspection object; inspection object an rotating arrangement for rotating the inspection object about a first rotational axis slanted to an, optical axis of X rays generated from the X-ray source; and an X-ray detecting arrangement where an X-ray image transmitted through the inspection object rotated by the inspection object rotating arrangement is rotated and superposed in synchronization with the inspection object rotated about second rotational axis in parallel to the first rotational axis, and the X-ray projection image outside of a focal plane perpendicular to the first rotational axis passing through an intersection of the optical axis and the first rotational axis is blurred and the X-ray tomographic image in the focal plane is detected as a clear image signal, thereby the X-ray tomographic image in the focal plane can be obtained based on the image signal obtained from the X-ray detecting arrangement.

14 Claims, 9 Drawing Sheets

X-RAY TOMOGRAPHY METHOD AND APPARATUS THEREOF

BACKGROUND OF THE INVENTION

The present invention relates to a tomography method by transmission X rays and an apparatus thereof, and more particularly to an X-ray tomography method and an apparatus thereof suitable for inspection and measurement of internal structure of a circuit board with multi-layer structure.

Laminography is known as technology of detecting a tomographic image in a certain aimed focal point within an object by transmission X rays in the prior art. This technology provides that two elements among three elements, an X-ray source, an object and a detector, are moved in synchronization and a tomographic image is detected.

As such technology, for example, that disclosed in Japanese patent application laid-open No. 116040/1984 is known well. This technology comprises a step of irradiating a body by a fixed radiation ray source where the body and a surface sensing the radiation rays and positioned next to the body with respect to the radiation ray source, both included within one plane, are rotated in the same direction synchronously about the first axis line and the second axis line respectively, and the first axis line and the second axis line are arranged in parallel to each other and the first axis line is transformed into the second axis line by analogous transformation in a positive ratio and the center of the radiation ray source, and the radiation ray source, the body and the sensing surface are arranged so as to remain to the exposed state by the radiation rays during the rotation; a step of transforming a plane including the section of the body into a plane including the sensing surface by analogous transformation transforming the first axis line into the second axis line; and a step where the plane forms an angle having the same value being equal to or more than 0° and less than 90° with respect to the axis line, and an image of at least a part of the section is formed onto the sensing surface, thereby tomography of the body is carried out along the section of the body included within one plane. To put it briefly, this technology relates to a method that an object and a film are rotated in synchronization and tomography is carried out.

In the above-mentioned prior art, however, since the film used in the detecting section, a detection image cannot be seen in real time. Also since the image is moved in parallel on the film plane, there is a problem in that even if a linear structure extending in the moving direction exists outside the focal plane, its image is not blurred but can be clearly detected.

Further in a known example disclosed in U.S. Pat. No. 4,926,452, (Japanese patent application laid-open No. 501411/1990), an electron beam is rotated and deflected thereby an X-ray source is moved in a circular pattern, and a fluorescent screen is advanced along a circular path thereby tomography is carried out.

In this technology in the prior art, since the electron beam is rotated and deflected, aberration is generated in the electron optic system and a fine electron beam cannot be obtained. Therefore a problem exists in that an X-ray source of minute focus cannot be obtained and the detection resolution is low.

SUMMARY OF THE INVENTION

In order to solve the above-mentioned problems in the prior art, an object of the present invention is to provide an X-ray tomography method and an apparatus thereof where a clear X-ray tomographic image is obtained regarding an arbitrary section of an inspection object and a defect of the inspection object in its complicated internal structure can be detected with high reliability.

Another object of the present invention is to provide an X-ray tomography method and an apparatus thereof where a clear X-ray tomographic image is obtained in real time regarding an arbitrary section of an inspection object and a defect of the inspection object in its complicated internal structure can be detected in real time with high reliability and stability.

A further object of the present invention is to provide an X-ray tomography method of a circuit board and an apparatus thereof where based on a clear X-ray tomographic image, inspection of a circuit connection portion such as a solder joint for a circuit board of multi-layer structure can be carried out automatically with high reliability.

That is, the present invention provides an X-ray tomography apparatus comprising an X-ray source for irradiating X rays to a inspection object; inspection object rotating arrangement for rotating the inspection object about the first rotational axis slanted with respect to the optical axis of X rays generated from the X-ray source; and X-ray detecting arrangement where an X-ray image transmitted through the inspection object rotated by the inspection object rotating arrangement is rotated and superposed in synchronization with the inspection object rotated about the second rotational axis in parallel to the first rotational axis, and the X-ray projection image outside the focal plane perpendicular to the first rotational axis passing through the intersection between the optical axis and the first rotational axis is made indistinct and the X-ray tomographic image in the focal plane is detected as a clear image signal, characterized in that the X-ray tomographic image in the focal plane can be obtained based on the image signal obtained from the X-ray detecting arrangement.

Also the present invention provides an X-ray tomography apparatus where the X-ray detecting arrangement comprises detecting arrangement for detecting an X-ray image transmitted through the rotated inspection object and converting it into an optical image, a focusing optical system for focusing the optical image outputted from the detecting arrangement, optical image rotating arrangement for rotating the optical image outputted from the detecting arrangement in synchronization with the inspection object rotated about the second rotational axis, and photo-electric converting arrangement for receiving the optical image focused by the focusing optical system and rotated by the optical image rotating arrangement so as to be superposed and outputting the X-ray tomographic image in the focal plane as a clear image signal.

The present invention provides an X-ray tomography apparatus where the detecting arrangement is constituted by an X-ray image intensifier.

The present invention provides an X-ray tomography apparatus where the detecting arrangement is constituted by a fluorescent screen for converting an X ray image into an optical image and an image intensifier for amplifying an optical image converted by the fluorescent screen.

The present invention provides an X-ray tomography apparatus where the X-ray detecting arrangement is constituted by X-ray image detecting arrangement for detecting an X-ray image transmitted through the rotated inspection object while being rotated and superposed in synchronization with the inspection object rotated about the second rotational axis and for outputting the X-ray tomographic image in the focal plane as a clear image signal.

The present invention provides an X-ray tomography apparatus where the X-ray detecting arrangement comprises X-ray image detecting arrangement for outputting an X-ray image transmitted through the rotated inspection object as an image signal, and adding arrangement for adding an image signal outputted from the X-ray image detecting arrangement while being rotated in synchronization with the inspection object rotated about the second rotational axis and for outputting the X-ray tomographic image in the focal plane as a clear image signal.

The present invention provides an X-ray tomography apparatus where the inspection object rotating arrangement comprises a Z stage for moving the inspection object in the direction of the first rotational axis, and an X-Y stage for moving the inspection object in the perpendicular direction of the first rotational axis.

The present invention provides an X-ray tomography apparatus where the X-ray source comprises an electron ray source for converging and irradiating electron rays, and a transmission type target for radiating X rays by the convergence electron rays irradiated from the electron ray source and capable of being moved to the convergence electron rays.

The present invention provides an X-ray tomography apparatus where the transmission type target is formed by an X-ray generating layer for generating X rays, and a support layer for supporting the X-ray generating layer.

The present invention provides an X-ray tomography method comprising a step of irradiating X rays irradiated from an X-ray source to an inspection object rotated about the first rotational axis slanted with respect to the optical axis of X rays generated from the X-ray source; a step of superposing an X-ray image transmitted through the rotated inspection object while being rotated about the second rotational axis in parallel to the first rotational axis in synchronization with the inspection object and making indistinct the X-ray projection image outside the focal plane perpendicular to the first rotational axis passing through the intersection between the optical axis and the first rotational axis and detecting the X-ray tomographic image in the focal plane as a clear image signal; and a step of obtaining the X-ray tomographic image in the focal plane based on the detected image signal.

The present invention provides an X-ray tomography method comprising a step of irradiating X rays irradiated from an X-ray source to an inspection object rotated about the first rotational axis slanted with respect to the optical axis of X rays generated from the X-ray source; a step of detecting an X-ray image transmitted through the rotated inspection object by detecting arrangement and converting it into an optical image; step of focusing the converted optical image and receiving it by photo-electric converting arrangement so as to be superposed while being rotated in synchronization with the inspection object rotated about the second rotational axis and making indistinct the X-ray projection image outside the focal plane perpendicular to the first rotational axis passing through the intersection between the optical axis and the first rotational axis and detect the X-ray tomographic image in the focal plane as a clear image signal; and a step of obtaining the X-ray tomographic image in the focal plane based on the detected image signal.

The present invention provides an X-ray tomography method where the inspection object is moved in the direction of the first rotational axis, and an X-ray tomographic image in an arbitrary section can be obtained.

The present invention provides an X-ray tomography method where the inspection object is positioned to the first rotational axis based on CAD data.

The present invention provides an X-ray tomography method where X rays from the X-ray source are radiated from the miniaturized point.

As above described, according to the present invention, effect as is provided that a clear X-ray tomographic image can be obtained regarding an arbitrary section of an inspection object, and a defect of the inspection object in complicated internal structure can be detected with high reliability from the clear X-ray tomographic image.

Also according to the present invention, an effect is provided that since a defect of the inspection object in complicated internal structure can be detected with high reliability, inspection of a circuit connection portion such as a soldering portion of a multi-layer substrate can be carried out automatically with high reliability.

DETAILED DESCRIPTION OF THE PREFERRED EMBODIMENTS

The principle of X-ray tomography according to the present invention will be described based on FIG. 1. As seen from FIG. 1, X rays 27 are generated radially from a fixed X-ray source 1, and object 2 for tomography is rotated about an rotational axis 5 slanted with respect to an optical axis 7. A detector 3 is rotated about a rotational axis 6 parallel to the rotational axis 5 in synchronization with the object 2. An X-ray tomographic image Of a focal plane 4 including an intersection between the optical axis 7 and the rotational axis 5 and being orthogonal with the rotational axis 5 is detected as a still image by the detector 3, but since an X-ray projection image of a plane other than the focal plane 4 is detected in superposition in a form that a rotating image is shifted, it becomes indistinct. Therefore an image of a structure outside the focal plane 4 can be made indistinct, and only the X-ray tomographic image on the focal plane 4 can be obtained clearly.

Figure 1:
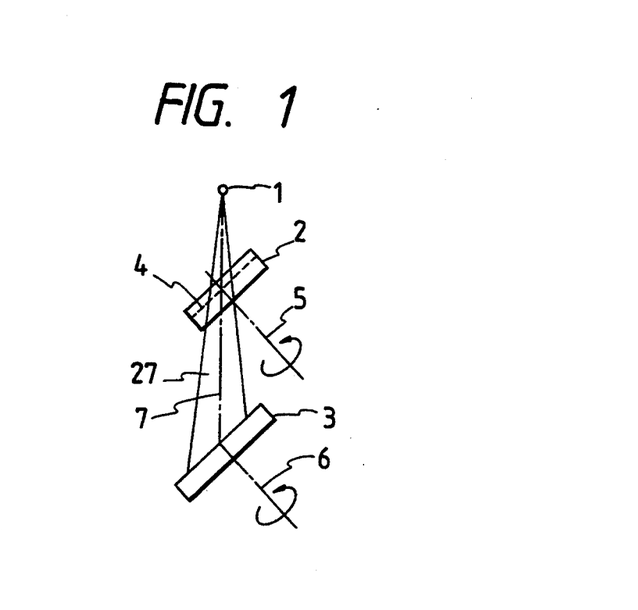
FIG. 1 is a diagram showing principle of an X-ray tomography method according to the invention.
Figure 2:
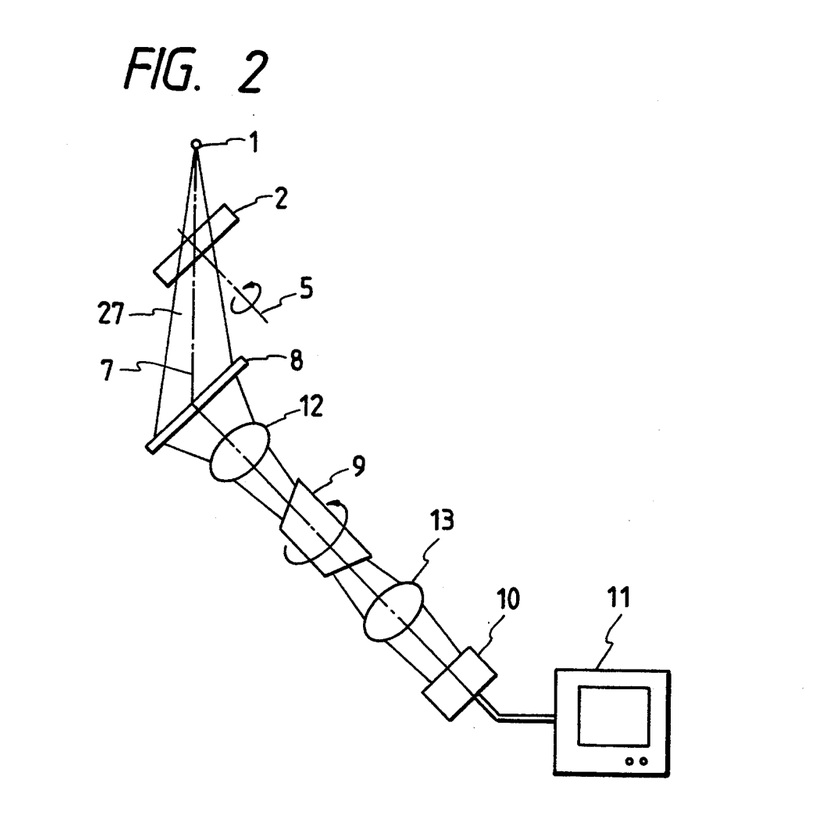
FIG. 2 is a diagram showing fundamental constitution of an X-ray tomography apparatus according to the invention.

An X-ray detector of the detector 3 or the like in FIG. 1 will be shown further concretely in FIG. 2. As seen from FIG. 2 X rays 27 are generated radially from the fixed X-ray source 1, and the object 2 for tomography is rotated about the rotational axis 5 slanted with respect to the optical axis 7. The X-ray detection system comprises arrangement 8 for converting an X-ray image into an optical image, optical image rotating arrangement 9 for rotating the optical image, and photo-electric converting means 10 for converting the optical image into an electric signal becoming a video signal, and optical transmission arrangement 12, 13 for transmitting the optical image are installed as optical supplementary arrangement. The optical image is rotated by the optical image rotating arrangement 9 in synchronization with the object 2, thereby the photo-electric converting arrangement 10 can detect the X-ray tomographic image of the object 2 in the focal plane 4 as a still optical image. Similar to FIG. 1, since the optical axis 7 and the rotational axis have a certain inclination, even if the detector 3 or the optical image rotating arrangement 9 is rotated, the X-ray projection image of the object 2 outside the focal plane is detected in a form that an image accompanied by rotation deviation is superposed, that is, in blurred state. If an electric signal obtained from the photo-electric converting means 10 is displayed as video information to the display arrangement 11, only a clear X-ray tomographic image in the focal plane 4 can be displayed at real time. After all, the object 2 outside the focal plane 4 can be blurred. Also in order to obtain an X-ray tomographic image with high resolution in the focal plane 4, in the case of the X-ray source 1 in radial state, the X-ray source 1 must be miniaturized close to a point source.

Figure 3:
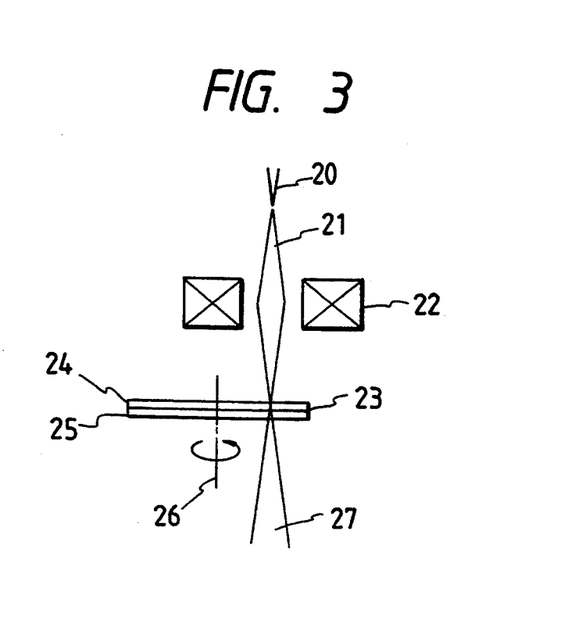
FIG. 3 is a diagram showing fundamental constitution of a minute X-ray source according to the invention.

A fundamental constitution of the minute focus X-ray source is shown in FIG. 3. The arrangement serves to improve the resolution, and in order to improve the resolution, half-shade indistinctness of a projection image must be made small and an X-ray source of minute focus size is necessary. The operation principle of the X-ray source is as follows.

If electron rays 21 generated from a cathode 20 are converged by a lens 22 and irradiated to a target 23, X rays 27 are generated. The transmission type target 23 is constituted by an X-ray generating layer 24 of heavy metal and a support layer 24 of light-weight element. In this case, for example, tungsten is selected as heavy metal and beryllium is selected as light-weight element. Then the electron rays 21 are converged sufficiently small and the X-ray generating layer 24 is thinned, thereby the minute focus size can be realized. Further, in order to prevent the target 23 from being broken by heat generated during collision of the electron rays 21, the transmission type target 23 is rotated about a rotational axis 26. Thus since the X-ray source is constituted so that the transmission type target 23 is rotated with eccentricity, the electron rays are irriadiated always to a new portion without dissipation on the X-ray generating layer 24 and therefore the miniaturization of the X-ray source without variation can be attained. Moreover, since the electron rays are not irradiated to one portion of the target, the thermal intensity can be increased. As a result, the X-ray tomographic image of high resolution in the focal plane can be detected with stability. Also since the transmission type target 23 is constituted by at least two layers, the X-ray generating layer 24 and the support layer 25, the X-ray generating layer is thinned and the scattering domain of electrons is limited thereby the miniaturization of diameter of the X-ray source can be attained, and further the mechanical intensity of the target can be secured by the support layer 25 and heat generated by irradiation of electron rays can be radiated from the support layer 25, thereby the X-ray source comprising the transmission type target being stabilized and miniaturized can be obtained. As a result, the X-ray tomographic image of high resolution in the focal plane can be detected with stability.

Figure 4:
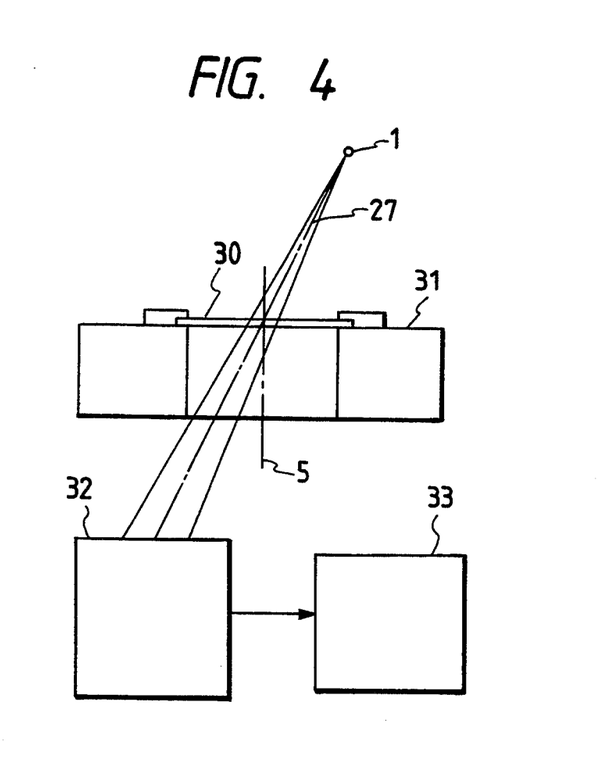
FIG. 4 is a diagram showing fundamental constitution of an automatic inspection apparatus within a circuit board of multi-layer structure according to the invention.

FIG. 4 shows a fundamental constitution of an automatic inspection apparatus to which an X-ray tomography apparatus according to the present invention is applied. As shown in FIG. 4, the automatic detecting apparatus comprises an X-ray source 1, a sample stage 31 to hold a circuit board 30, a detecting section 32 for detecting an X-ray tomographic image on the circuit board 30, and a defect decision section 33. The sample stage 31 has a rotation function of rotating and driving the circuit board 30 about the rotational axis 5, and a function of moving the circuit board 30 to change the detection visual field in a step-and-repeat wise manner. The procedure of inspection is as follows. First, the focal plane is set to a section having soldering portion or the like being the inspection object, and the tomographic image is detected. Next, the detected image is processed in the defect decision section 33, and the defect portion is extracted. Next, the sample stage 31 is moved and the detection visual field is changed, and the tomographic image in the changed detection visual field is detected and the defect portion is extracted. Similar operations are repeated and the whole surface of the circuit board 30 is inspected. In addition, the detecting section 32 has the constitution shown in FIG. 2.

Embodiments of the present invention will be described referring to the accompanying drawings as follows. In the following description, components deemed the same as each component hereinbefore described are designated by the same reference numerals and the overlapped description shall be omitted.

Figure 5:
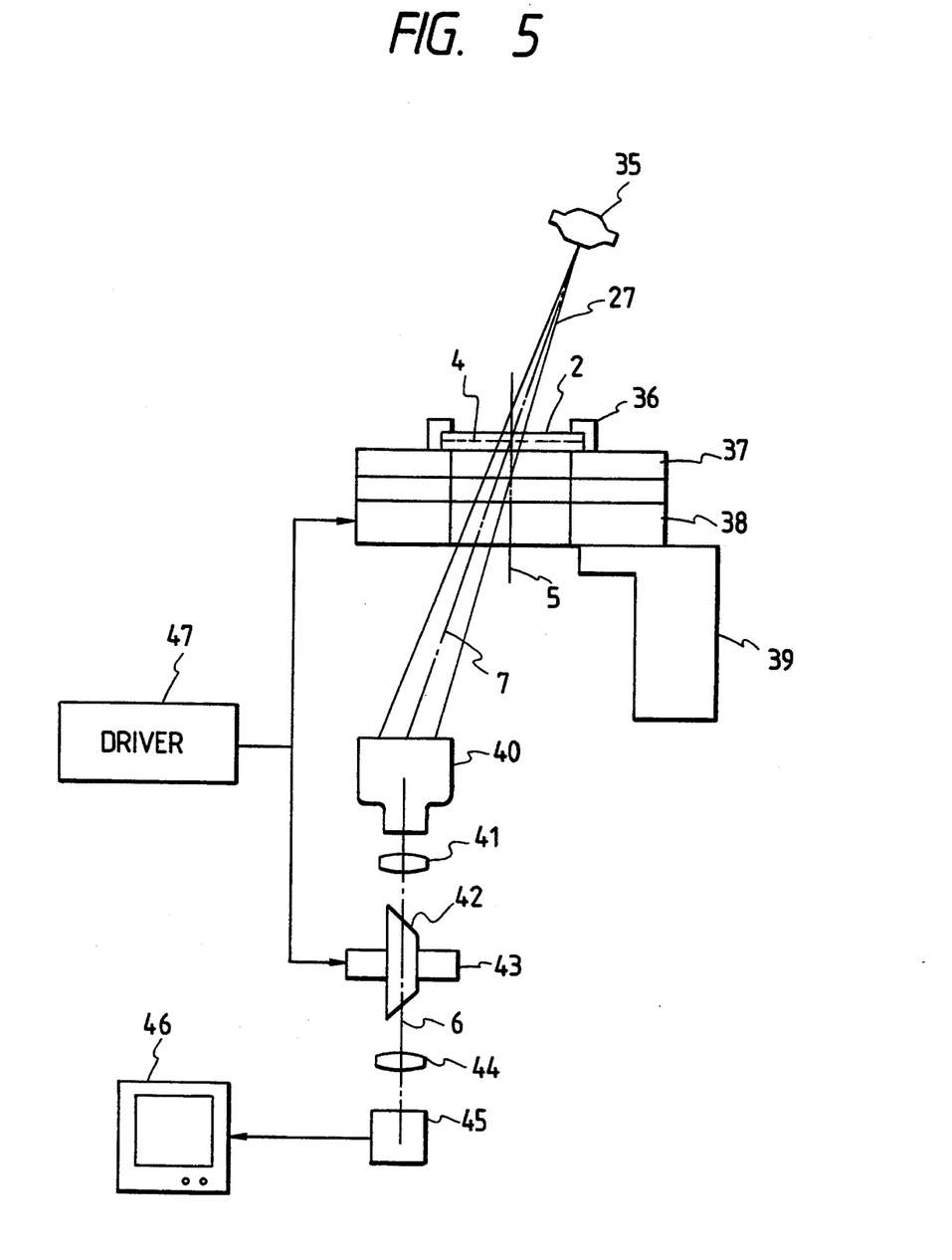
FIG. 5 is a diagram showing constitution of an embodiment of an X-ray tomography apparatus according to the invention.

FIG. 5 is a diagram showing an embodiment of a tomography apparatus according to the present invention. The tomography apparatus is basically constituted by an X-ray detection system, a sample stage system and a display system. The sample stage system is constituted by an XY stage 37, a rotary stage 38 and a stage 39, and an object 2 such as a circuit board is held to the XY stage 37 through a chuck 36. Each of stages 37, 38, 39 is of transmission type which does not intercept an optical axis 7. The X-ray detection system is constituted from the side of an X-ray tube 35 being an X-ray source 1 by an X-ray image intensifier 40, a lens 41, an image rotator 42, a lens 44 and a solid image pickup element (for example CCD) 45. Also the display system comprises a display 46.

In the tomography apparatus broadly constituted in such manner, X rays 27 generated from the X-ray tube 35 go away to the side of the object 2 and are transmitted through the object 2 and incident to the X-ray image intensifier 40. The X-ray image is amplified in brightness by the X-ray image intensifier 40 and converted into an optical image. The optical image is focused to the CCD 45 by the lens 41 and the lens 44, and the video signal of the clear X-ray tomographic image in the focal plane 4 is held in the CCD 45 and displayed in the display 46.

As above described, since the X-ray image is detected by the X-ray image intensifier 40 and the converted optical image is rotated by the image rotator 42 in synchronization with the object 2 and the X-ray tomographic image in the focal plane 4 being still in the stored form is received by the CCD 45 and detected as the video signal, the image of the structure in a plane other than the focal plane can be blurred and the clear X-ray tomographic image in the focal plane 4 can be detected at in real time.

A procedure to obtain the tomographic image is shown as follows. The object 2 and the X-ray image intensifier 40 are positioned so that respective rotational axes 5, 6 are in parallel to each other, and the optical axis 7 is slanted with respect to the rotational axis 5. The object 2 is rotated by the rotational stage 38, and at the same time the image rotator 42 is rotated by the rotational stage 43.

In the image rotator 42, a double prism (image rotation prism) and an image rotation mirror constituted by three mirrors are mentioned respectively and both can be used. When the double prism is used, in order to suppress occurrence of aberration, rays of light being incident to the double prism must be parallel rays. Rays collimated by the lens 41 are entered to the double prism and focused to the CCD 45 by the lens 44. FIG. 5 shows an example using the double prism. When the image rotation mirror is used, incident rays need not be necessarily parallel rays. When the image rotator 42 is rotated one turn, the optical image is rotated two turns. Consequently, control is carried out in the driver 47 so that speed of the rotational stage 43 becomes a half of speed of the rotational stage 38, and the object 2 and the optical image are rotated in synchronization. As such control, for example, a stepping motor is used and frequency of drive pulse is controlled to 2: 1, or a motor with encoder is used and rotation is supervised and rotation of the motor may be controlled in synchronization.

Next, the storage time of the CCD 45 is made a time required for the rotational stage 38 to rotate one turn, and every time the image is rotated one turn, the image is read out. Consequently, since the image outside the focal plane 4 is rotated on the surface of the CCD 45 and made indistinct, the X-ray tomographic image in the focal plane 4 only can be obtained. Of course, the reading period of the CCD 45 can be lengthened more than one turn of the image, however, since thermal noise becomes much in use at exposure for a long time, it is effective that the CCD 45 is cooled and thermal noise is decreased. Since the focal plane 4 is a plane including the intersection between the optical axis 7 and the rotational axis 5 of the rotational stage 38, if the Z stage 39 to carry out the moving in the vertical direction is moved up and down, the tomographic image of the object 2 in an arbitrary plane can be obtained. Also the visual field can be changed arbitrarily by moving the XY stage 37. Thereby even in the circuit board of multi-layer structure, inspection of the tomographic plane in an arbitrary position becomes possible.

The X-ray tube 35 is preferably a micro focus type so as to improve the detection resolution. When the X-ray tube 35, the sample stage and the X-ray detection system are made movable respectively, change of the detection magnification and adjustment of focusing range becomes possible. In this case, if the sample stage comes close to the X-ray tube 3, the magnification becomes high, and if both are separated from each other, the magnification becomes low. Also when the angle between the optical axis 7 and the rotational axis 5 is made large, the focusing range becomes narrow, and when the angle is made small, the focusing range becomes wide.

Figure 6:
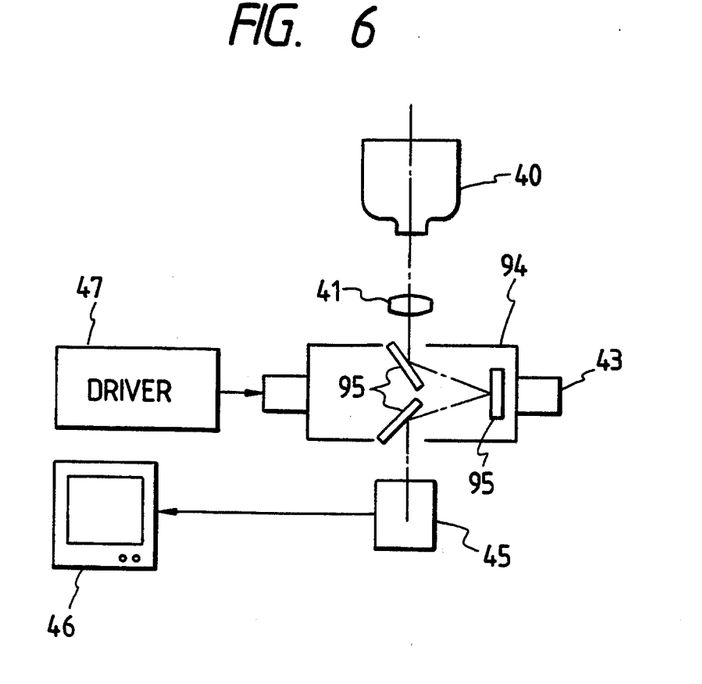
FIG. 6 is a diagram showing another example of an image rotator.

FIG. 6 shows an embodiment where an image rotation mirror constituted by three mirrors is used as the image rotator 42. An image rotation mirror 94 is constituted by three mirrors 95. In the image rotation mirror, since incident rays need not be made parallel rays being different from the double prism, the optical system to focus the output image of the image intensifier 40 to the CCD 45 need not be separated into a collimator lens and an imaging lens, but can be realized by one lens 41.

Regarding the X-ray detection system to be used in the X-ray tomography apparatus, in addition to the above-mentioned embodiment, several embodiments can be mentioned and therefore other embodiments in the X-ray detection system will be described subsequently. The following embodiment of the X-ray detection system as it is, becomes an X-ray tomography apparatus, when the corresponding component is exchanged by the X-ray detection system shown in FIG. 5 (hereinafter referred to also as the first embodiment of the X-ray detection system).

Figure 7:
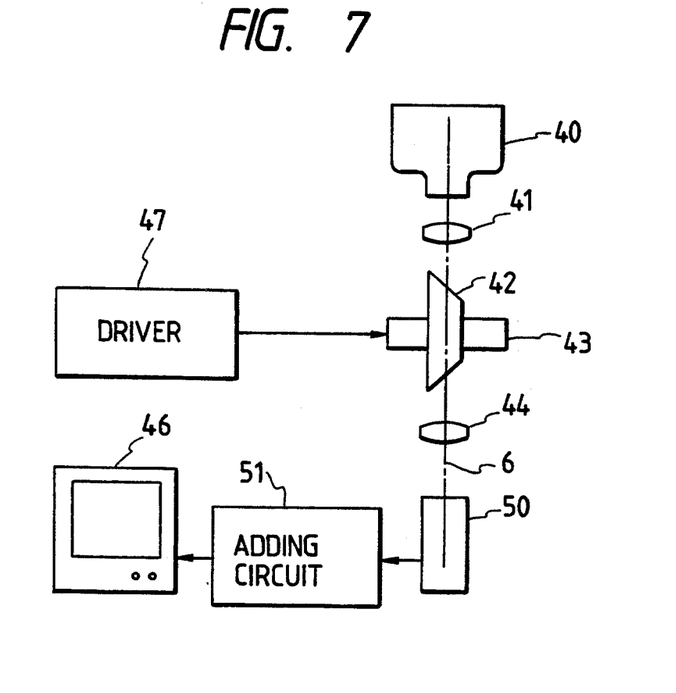
FIG. 7 is a diagram showing constitution of a second embodiment of an X-ray detection system.

FIG. 7 shows a second embodiment of the X-ray detection system. In this embodiment, an X-ray image is converted by an X-ray image intensifier 40 into an optical image, which is focused to a detection surface of an image pickup tube 50 by lenses 41, 44. An image rotator 42 is inserted at the midway of the optical path, and can be rotated through a rotational stage 43. Thereby the converted optical image is rotated. The rotational stage 43 to rotate the image rotator 42 is controlled by a driver 47 so that it is rotated at a half speed of a rotational stage 38 to rotate the object. Further, the optical image is converted by the image pickup tube 50 into an electric signal (video signal) becoming video information. Since the image pickup tube 50 outputs an image at TV rate, i.e., every 1/30 seconds, the image in a time for the optical image to rotate one turn is added by an adding circuit 51. For example, when the period of rotation is made 0.5 seconds, 15 sheets of the image are added. For example, a video signal is converted by an A/D converter into a digital signal and sampled, and the adding circuit 51 adds 15 sheets of image to a frame memory and an image signal of a clear X-ray tomographic image in the focal plane 4 can be obtained and returned to a video signal by a D/A converter and the image signal of the added X-ray tomographic image is displayed to the display 46.

Figure 8:
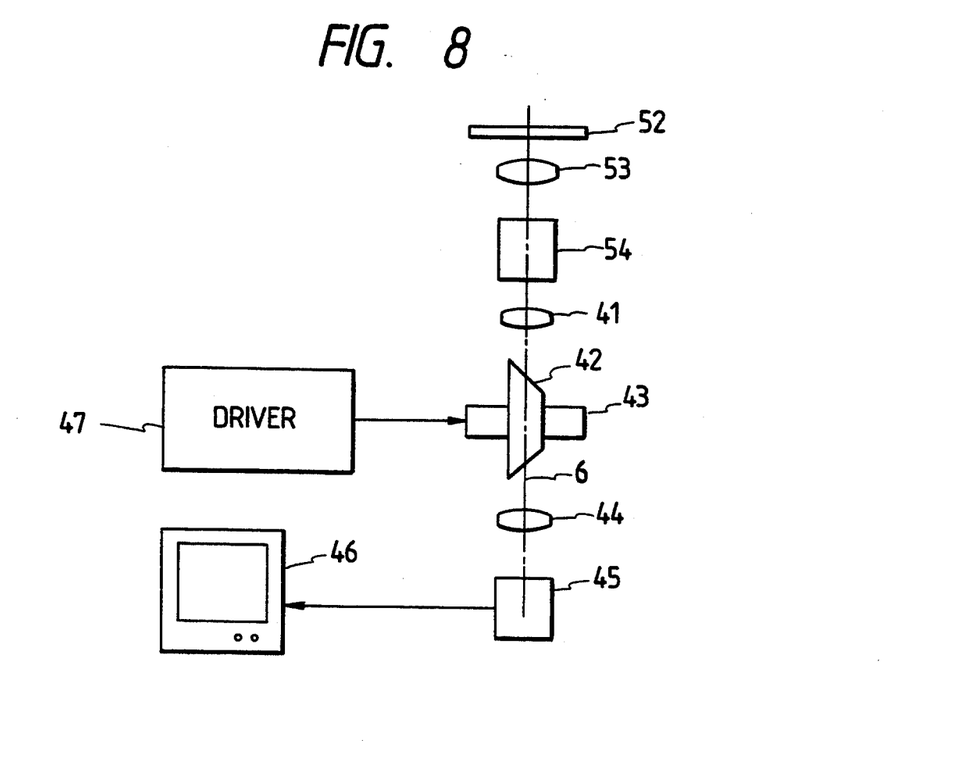
FIG. 8 is a diagram showing constitution of a third embodiment of an X-ray detection system.

FIG. 8 shows a third embodiment of the X-ray detection system. In this embodiment, an X-ray image is converted by a fluorescent screen 52 into an optical image. The X-ray image intensifier 40 used in the first and second embodiments has the image distortion of about 5%, and the resolution is as low as about 5 lp (line pair)/mm. However, the fluorescent screen 52 has no image distortion, and the resolution of about 20 lp/mm can be obtained. As the fluorescent screen 2, in order to improve the resolution, a monocrystalline scintillator, for example, CsI(Tl) (thallium activation cesium iodide) or $CaF_2(Eu)$ or the like being ground to thickness of about 0.4 mm, is preferable. Also since light excited by the X-ray irradiation is week, an optical image of sufficient light quantity cannot be obtained. Consequently, the image of the fluorescent screen 52 is focused to an image intensifier 54 by a lens 53 and brightness is amplified by the image intensifier 54. As the image intensifier 54, a proximity type image intensifier without image distortion is preferable. In this case, it is needless to say that an image fiber may be used in place of the lens 53. The optical image amplified by the image intensifier 54 is focused to a CCD 45 by a lens 41 and a lens 44, and the image is rotated by an image rotator 42 at the midway of the optical path. The image is converted into an electric signal (video signal) by the CCD 45, and an image signal of a clear X-ray tomographic image in the focal plane 4 is obtained and displayed to a display 46. The constitution after the image intensifier 4 is the same as that of the first embodiment (FIG. 5) of the X-ray detection system. In this case, an image pickup tube as shown in the second embodiment (FIG. 7) of the X-ray detection system may be used in place of the CCD 45.

Figure 9:
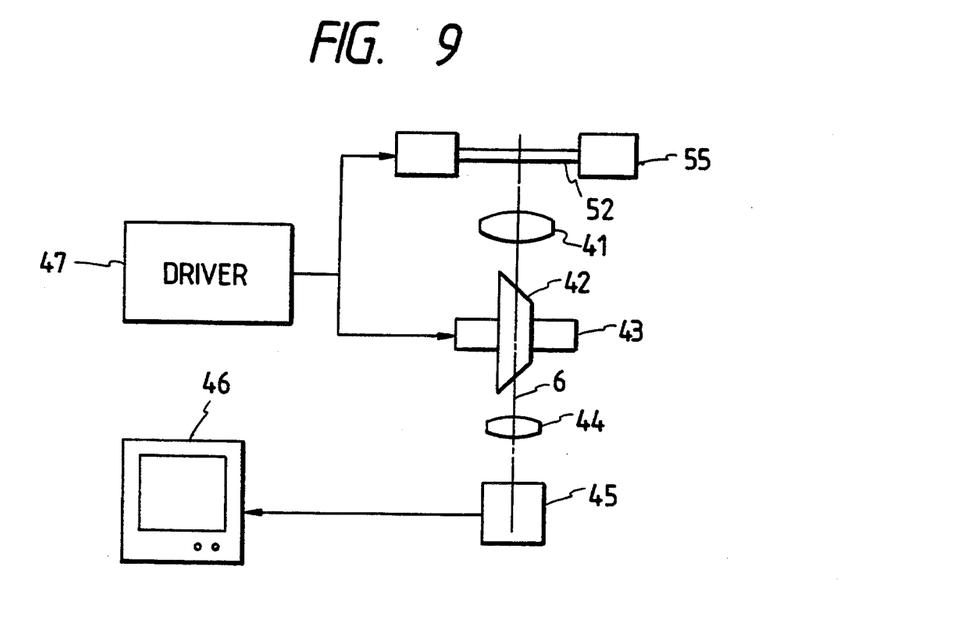
FIG. 9 is a diagram showing constitution of a fourth embodiment of an X-ray detection system.

FIG. 9 shows a fourth embodiment of the X-ray detection system. In this embodiment, an X-ray image is converted into an optical image by a fluorescent screen 2 in similar manner to the third embodiment of the X-ray detection system. The fluorescent screen is constituted rotatable by a rotational stage 55, and is controlled by a driver 47 so that it is rotated at the same speed as that of an object 2. Since the fluorescent screen 52 and the object 2 are rotated in synchronization, an image of the object 2 in a focal plane 4 stands still on the fluorescent screen 52. Therefore a material with long afterglow time is used in the fluorescent screen 52, thereby the image in the focal plane 4 is detected clearly. An optical image on the fluorescent screen 52 is focused to a CCD 45 by a lens 41 and a lens 44, and the image is rotated by an image rotator 42 inserted at the midway of the optical path. When a time required for the image to rotate one turn is made an exposure time, the CCD 45 displays a detected electric signal (video signal) to a display 46. Constitution after the lens 41 is similar to that of the first embodiment (FIG. 5) of the X-ray detection system. An image intensifier may be inserted at the midway of the optical path so as to amplify the brightness. Also in place of the CCD 45, an image pickup tube as shown in the third embodiment (FIG. 7) of the X-ray detection system may be used. The image pickup tube with high sensitivity is preferable, for example, an SIT (Silicon Intensified Target) tube, an avalanche multiplying type image pickup tube or an ICCD (Image Intensified CCD) camera or the like is mentioned.

Figure 10:
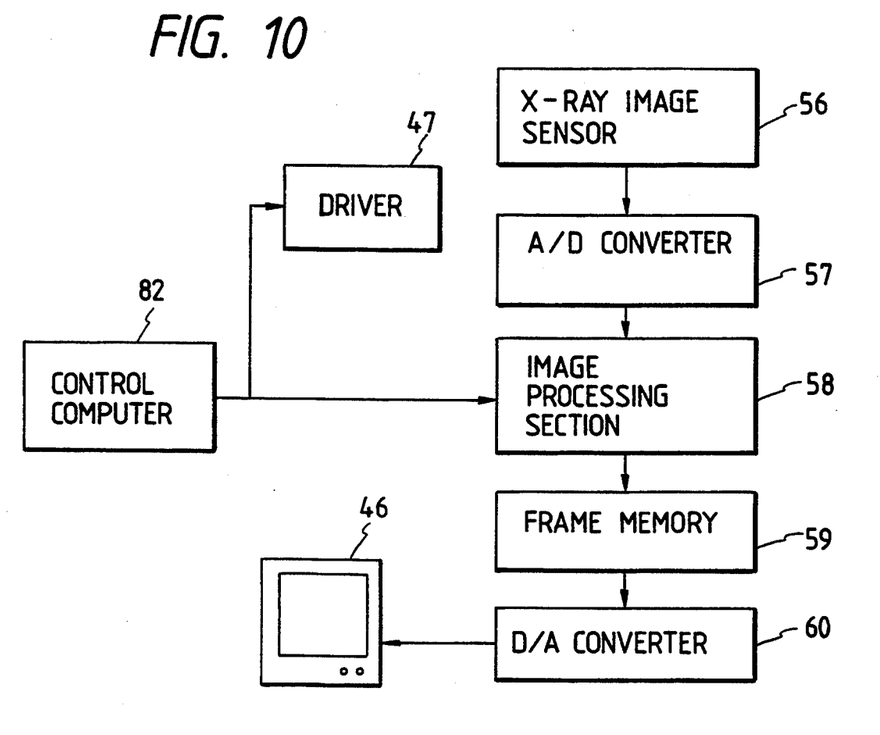
FIG. 10 is a diagram showing constitution of a fifth embodiment of an X-ray detection system.

FIG. 10 shows a fifth embodiment of the X-ray detection system. This embodiment is an example where an image rotator is not used and an image is rotated by image processing. The X-ray detection system in this embodiment is basically constituted by an X-ray image sensor 56, and an A/D converter 57, an image processing section 58, a frame memory 59 and a D/A converter 60.

In such X-ray detection system, at first, the X-ray image is converted into an electric signal (video signal) by the X-ray image sensor 56. The X-ray image sensor 56 outputs the electric signal (video signal) at TV rate, i.e., every 1/30 seconds. This video signal is converted into a digital signal by the A/D converter 57, thereby a digital image is obtained. Next, the obtained digital image is rotated in the image processing section 58 by an angle synchronized with rotation of the object, and the image corresponding to one rotation is added to the frame memory 59. For example, when the object is rotated in period of 2 seconds, the image is rotated by 6° in 1/30 seconds. Therefore the image detected first is made rotation of 0°, and the image detected at the second time is rotated by 6° and the image detected at the n-th time is rotated by $6 \times (n-1)°$. Thus images until that detected at the 60-th time are added to the frame memory 9, and an image signal of a clear X-ray tomographic image in the focal plane 4 can be obtained. A digital image accumulated in such manner is converted into an analog video signal by the D/A converter 60 and displayed in a display 46. The X-ray image intensifier 56 in this embodiment can be replaced, for example, by a system in combination of an X-ray vidicon, an X-ray image intensifier and an image pickup tube, a system in combination of a fluorescent screen and an image pickup tube, or the like.

Figure 11:
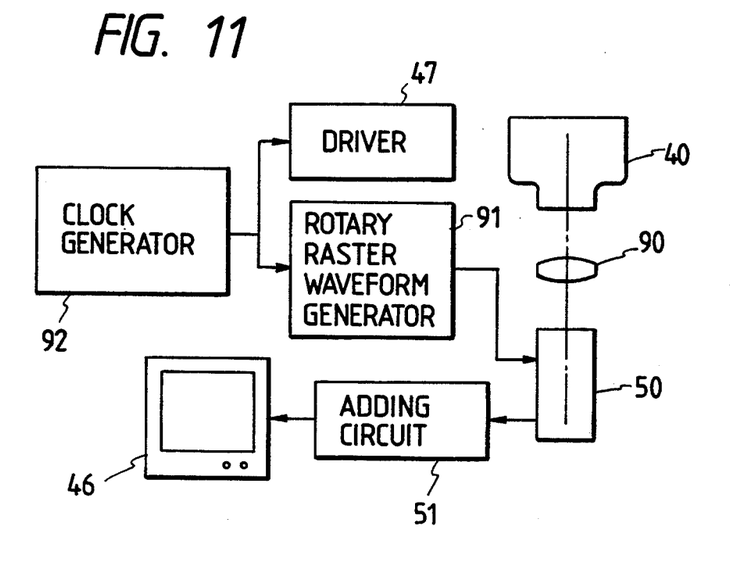
FIG. 11 is a diagram showing constitution of a sixth embodiment of an X-ray detection system.

FIG. 11 shows a sixth embodiment of the X-ray detection system. This embodiment is an example where an image pickup tube in rotary raster scanning is used. An X-ray detection system in this embodiment is basically constituted by an X-ray image intensifier 40, a lens 90, an image pickup tube 50, a rotary raster waveform generator 91, a clock generator 92, an adding circuit 51 and a driver 47.

In this embodiment, an X-ray image is converted into an optical image by the image intensifier 40, and the optical image is focused to a detection surface of the image pickup tube 50 by the lens 90. The image pickup tube 50 is subjected to rotary raster scanning by drive waveform generated in the rotary raster waveform generator 91. Therefore, a rotary image is detected as a still image. In order that rotation speed of the rotary stage 38 to rotate the object 2 shown in the first embodiment (FIG. 5) of the X-ray detection system and speed of rotary raster scanning of the image pickup tube 50 are synchronized, the rotary raster waveform generator 91 and the driver 47 are driven according to a clock signal from the clock generator 92. Regarding an image detected by the image pickup tube 50, an image corresponding to time for one rotation of an image or more is added, and an image signal of a clear X-ray tomographic image in the focal plane 4 is obtained and displayed to a display 46. In this embodiment, in place of the X-ray image intensifier 40, a fluorescent screen or combination of a fluorescent screen and an image intensifier can be used.

Figure 12:
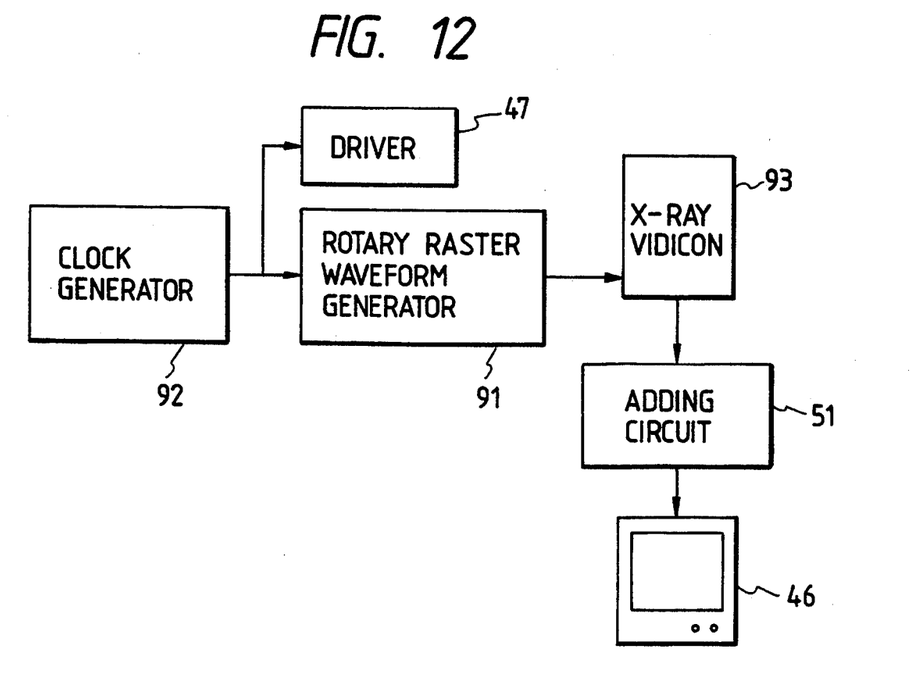
FIG. 12 is a diagram showing constitution of a seventh embodiment of an X-ray detection system.

FIG. 12 shows a seventh embodiment of the X-ray detection system. An X-ray detection system in this embodiment is basically constituted by an X-ray vidicon 93, an adding circuit 51, a clock generator 92, a rotary raster waveform generator 91 and a driver 47.

In this embodiment, at first, an X-ray image is detected by the X-ray vidicon 93. Then rotary raster scanning is carried out according to drive waveform generated in the rotary raster waveform generator 91, thereby a rotary image is detected as a still image. In order that rotation speed of the rotary stage 38 (FIG. 5) and speed of rotary raster scanning of the imagine pickup tube 50 are synchronized, the rotary raster waveform generator 91 and the driver 47 are driven according to a clock signal from the clock generator 92. An image detected by the image pickup tube 50 is added by an image corresponding to time required for one rotation of an image or more in the adding circuit 51, and an image signal of a clear X-ray tomographic image in the focal plane 4 is obtained and displayed in a display 46.

Further, in order to improve detection resolution of an X-ray tomography apparatus according to the present invention, miniaturization of an X-Ray source is necessary. Therefore, in addition to miniaturization of an electron beam to be irradiated, a target must be made thin-film transmission type. Embodiments regarding miniaturization of the X-ray source in this manner will be described based on FIG. 13 and FIG. 14.

Figure 13:
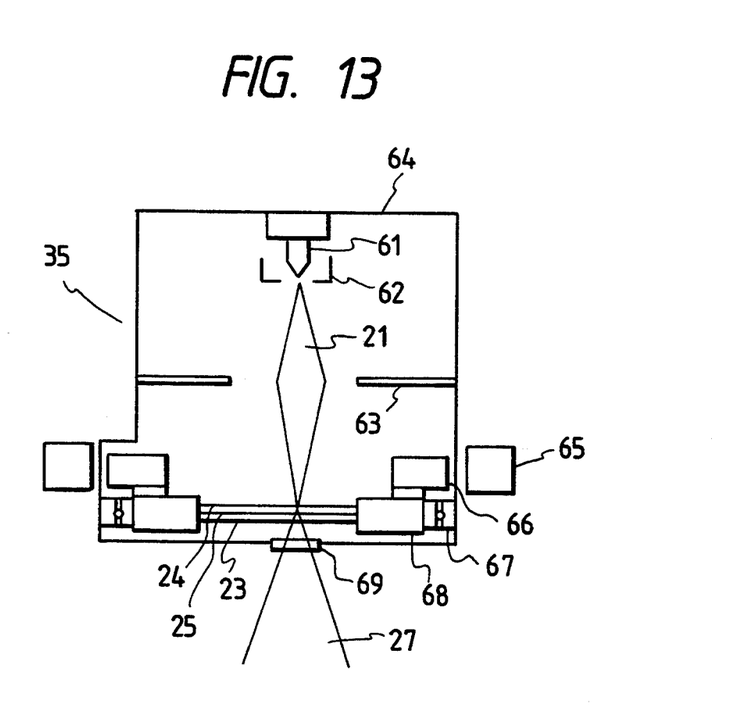
FIG. 13 is a diagram showing constitution of a first embodiment of a minute focus X-ray tube according to the invention.

FIG. 13 shows an embodiment of an X-ray tube to obtain minute focus type. The X-ray tube is mainly constituted by a filament 61, a Wehnelt cylinder 62, an electric field lens 63, and a target 23 in multi-layer structure of an X-ray generating layer 24 and a support layer 25, and is enclosed within a glass bulb 64. X rays 27 can go away from an X-ray transmission window 69 provided on a portion of the glass bulb 64 opposed to the target 23.

That is, in the X-ray tube, electron rays 21 generated from the filament 61 are converged to the target 23 by the Wehnelt cylinder 62 and the electric field lens 63. The target 23 is fixed at its circumference to a bearing shaft 68, and has structure rotatable by a bearing 67. A stator 65 is installed outside the glass bulb 64, and when the stator 65 is excited, a rotor 66 within the glass bulb 64 is rotated thereby the target 23 is rotated. X rays 27 generated in the target 23 by irradiation of the electron rays 21 are taken out of the X-ray transmission window 69 as above described.

In order to miniaturize diameter of the X-ray source, beam diameter of the electron rays 21 to be irradiated to the target 23 must be miniaturized. Therefore the filament 61 is preferably made of material of high luminance, and in comparison to a tungsten filament used conventionally, $LaB_6$ (lanthanum hexaboride) filament is preferable and has merit of long life. Or an electric field radiation type filament may be used. Also the electric field lens 63 to converge the electron rays 21 is preferably constituted by plural pieces so as to obtain minute electron beam diameter.

Electrons being incident to the target 23 of multi-layer structure collide with atoms and are scattered and spread to the inside of the target. Amount of the spread in the tube voltage 100 kV is about 5 $\mu m$, and therefore even if the electron beam is converged to one point (spread 0), diameter of the X-ray source becomes 5 $\mu m$ or more. In order to miniaturize diameter of the X-ray source, scattering domain of electrons must be limited using a target of thin film. In the present invention, the target 23 is made multi-layer structure of the X-ray generating layer 24 and the support layer 25. The X-ray generating layer 24 is preferably made of tungsten W or alloy of tungsten and thorium, and its film thickness is 0.5 to 5 $\mu m$ depending on aimed diameter of the X-ray source. The support layer 25 is preferably made of beryllium being light-weight element, and its thickness may be about 10 $\mu m$. The support layer 25 serves to increase the mechanical strength of the target 23 and to liberate heat generated by irradiation of the electron rays 21. Further, in order that the electron rays 21 are not irradiated to one position of the target 23, the target 23 is not rotated by the stator 65 and the rotor 66 thereby strength against heat is increased and breakage is prevented.

Figure 14:
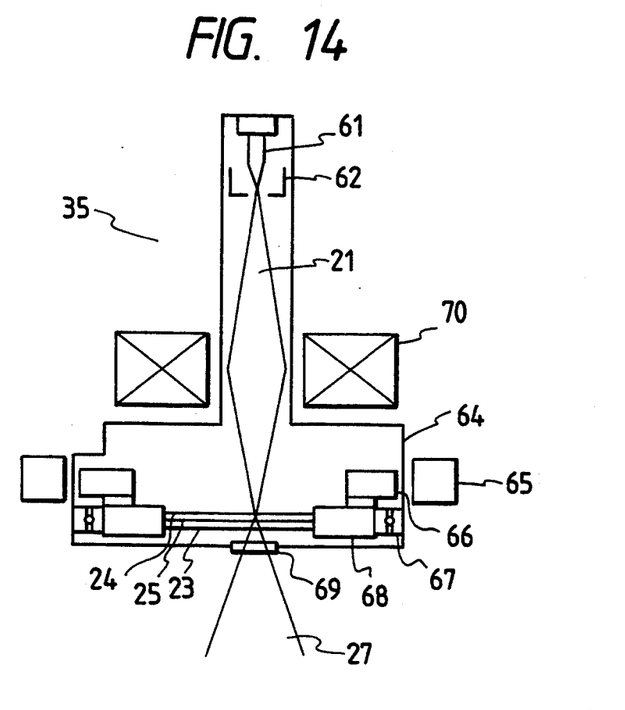
FIG. 14 is a diagram showing constitution of a second embodiment of a minute focus X-ray tube according to the invention.

The embodiments shown in FIG. 13 (hereinafter referred to also as the first embodiment of the X-ray tube) user an electric field lens in an electron lens, and FIG. 14 shows an embodiment using an electromagnetic lens. In this embodiment, electron rays 21 generated from a filament 61 are converged to a target 23 by a Wehnelt cylinder 62 and a magnetic field lens 70. The target 23 is fixed at its circumference to a bearing shaft 68 and has structure rotatable by a bearing 67, and it is rotated and driven by a stator 65 and a rotor 66 in similar manner to the first embodiment of the X-ray tube. The inside of the glass bulb 64 is at high vacuum. Although the electric field lens 63 in the first embodiment of the X-ray tube is at the inside of the glass bulb 64, the glass bulb 64 passes through the center of the electromagnetic lens 70 in this embodiment. Therefore when the life of the filament 61 or the target 23 has expired, only the glass bulb 64 may be exchanged and the electromagnetic lens 70 can be used as it is.

Also in similar manner to the first embodiment of the X-ray tube, the electromagnetic lens 70 is preferably constituted by plural pieces so as to obtain minute focus size.

Figure 15:
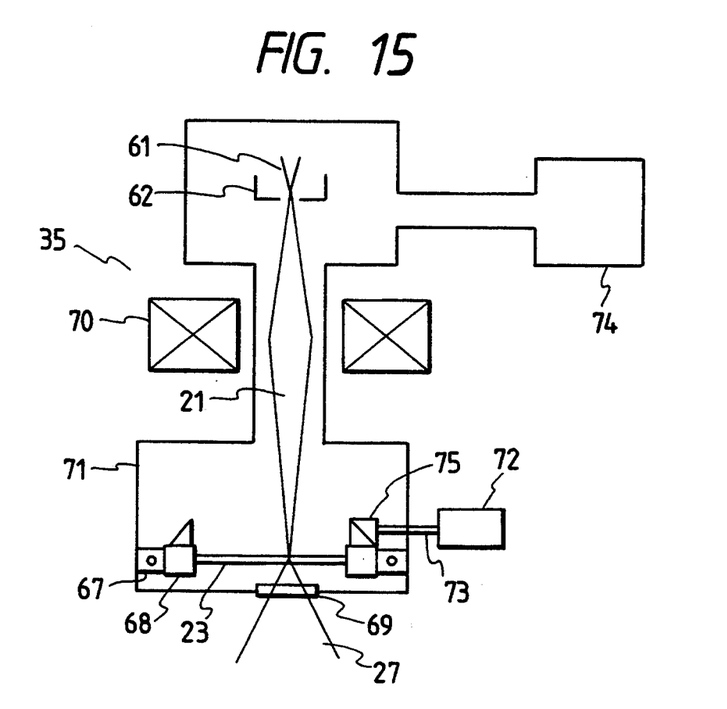
FIG. 15 is a diagram showing constitution of a third embodiment of a minute focus X-ray tube according to the invention.

The above-mentioned two embodiments are that of a closed type X-ray tube where various elements are enclosed within the glass bulb 64, but FIG. 15 shows an embodiment of an open type X-ray tube In this embodiment of the open type X-ray tube, a vacuum container 71 is used in place of the glass bulb 64 in the first embodiment of the X-ray tube, and air within the container is drawn by a vacuum pump 74 and the vacuum state is held, and combination of the stator 65 and the rotor 66 is replaced by combination of a motor 72 and a gear 75, and further a magnetic field lens 70 is used in place of the electric field lens 63.

In this embodiment, electron rays 21 generated from a filament 61 are converged to a target 23 by a Wehnelt cylinder 62 and a magnetic field lens 70. The target 23 is fixed at its circumference to a bearing shaft 68, and has structure rotatable by a bearing 67. The target 23 rotates the motor 72 outside the vacuum container 71, and is rotated through a rotation introducing shaft 73 and the gear 75. It is needless to say that the target 23 may be rotated by a stator and a rotor in similar manner to the first embodiment of the X-ray tube. X rays 27 generated in the target 23 by irradiation of the electron rays 21 are taken out of the X-ray transmission window 69. The vacuum container 71 is held to the vacuum state by the vacuum pump 74. Structure of the target 23 is the same as that of the first embodiment of the X-ray tube shown in FIG. 12.

As an X-ray source, synchrotron radiation rays (SR rays) may be also used so as to raise the detection resolution. In this case, since the SR rays are parallel rays, half-shade indistinctness is not produced and therefore the resolution is not degraded.

Figure 16:
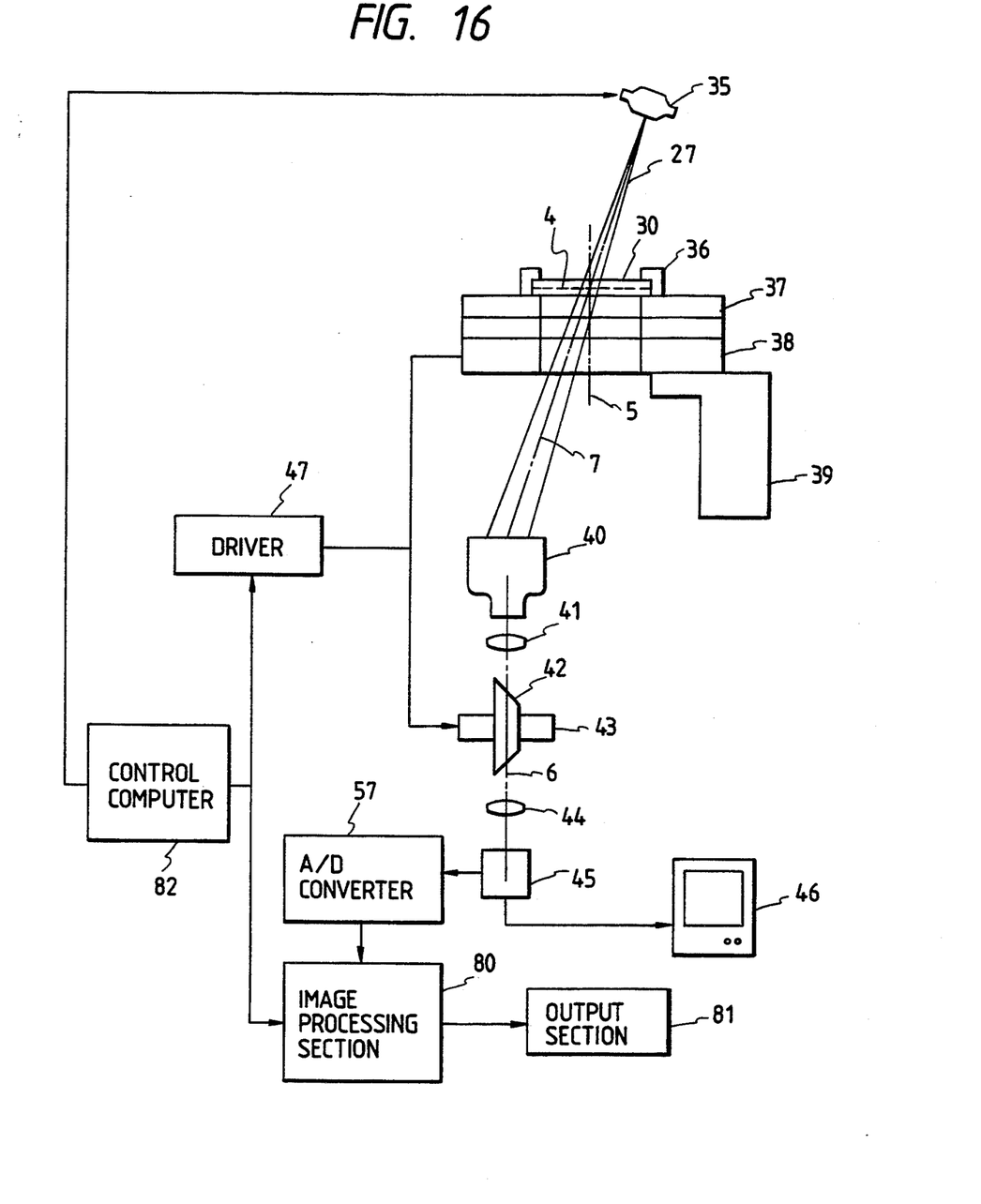
FIG. 16 is a diagram showing constitution of an embodiment of an automatic inspection apparatus within a circuit board according to the invention.

Next, FIG. 16 shows an embodiment of an automatic inspection apparatus of a soldering portion of a circuit board or a circuit connection portion, using an X-ray tomography apparatus according to the present invention. In this automatic inspection apparatus, parts of the X-ray tomography apparatus from an X-ray tube 3 to a CCD 45 are the same as those of the first embodiment of the X-ray detection system described in FIG. 5, and further an A/D converter 7, an image processing section 80, a result output section 81 and a control computer 82 are added thereto.

In this automatic inspection apparatus, a video signal outputted from the CCD 45 is made a digital image by the A/D converter 57, and a defect portion is extracted in the image processing section 80, and position or sort of the defect is outputted from the result output section 81. The control computer 82 controls the operation of the whole inspection apparatus and supervises the inspection procedure.

The inspection procedure is shown as follows.

(1) A circuit board 30 is set to stages.

(2) XY stage 37 and Z stage 39 are moved through a driver 47 according to command from a control computer 82, and X rays 27 are irradiated from an X-ray tube 35, and the circuit board 30 is positioned based on information displayed in display arrangement 46 so that an inspection portion is entered in the visual field. It is needless to say that the circuit board 30 may be positioned, based on other AD data such as design information or detection information such as positioning mark or the like.

(3) While a target 23 of the X-ray tube 35 is slowly rotated with eccentricity according to command from the control computer 82, X rays 27 are radiated from a minute portion of the target 23 to the circuit board 30.

(4) According to drive control from a driver 47, a rotary stage 38 with the circuit board 30 held thereon and a rotary stage 43 with a double prism 42 attached thereto are rotated in synchronization. That is, the circuit board 30 is rotated about a rotational axis 5 slanted with respect to an optical axis 7 by the rotary stage 38. An X-ray projection image detected by an X-ray image intensifier 40 is converted into an optical image and focused onto a CCD 45 by lenses 41, 44, and the optical image is rotated in synchronization with rotation of the circuit board 30 by a double prism 42 rotating about a rotational axis 6. The CCD includes intersection between the optical axis 7 and the rotational axis 5, and an X-ray tomographic image in an inspection portion of a plane (focal plane) 4 perpendicular to the rotational axis 5 is detected as a signal in superposed state (stored state) of a still optical image. Since the CCD 45 detects a signal in state that a rotary image with an X-ray projection image outside the focal plane 4 shifted a little is superposed, an image of a structure of the circuit board 30 outside the focal plane 4 can be blurred and only an X-ray tomographic image in the focal plane 4 of the inspection portion can be obtained clearly. A signal stored in the CCD 45 is read out in synchronization with rotation of the circuit board 30, and converted into a digital image signal by the A/D converter 57 and stored as an X-ray tomographic image in the image processing section 60.

(5) Next, according to command from the control computer 82, the Z stage 39 is moved gradually through the driver 47, and the CCD 45 detects necessary sheets of an X-ray tomographic image in the inspection portion in similar manner to the above, and stores the detected image as a digital image signal through the A/D converter 57 in the image processing section 80.

(6) From n sheets of an X-ray tomographic image, a decision is effected in the image processing section 80 regarding whether an article is good or not. Since a soldering portion is high in X-ray absorbing rate, it is detected as dark shade. The detected shade is compared with that of a good article, or it is compared with that calculated based on the design data, or the feature quantity of the detected shade is calculated, thereby decision of defect is effected.

(7) Next, according to command from the control computer 82, the XY stage 37 is moved through the driver 47 and an inspection portion is changed. Processings from (4) to (6) are repeated. Further, the XY stage 37 is moved, and inspection of the whole surface of the circuit board 30 is carried out.

(8) As above described, the image processing section 80 carries out the defect inspection regarding the circuit board 30 according to command from the control computer 82, and position and sort of the defect being inspection results are outputted to the result output section 81.

(9) The inspected circuit board 30 is removed from the XY stage 37.

When such inspection procedure is taken, a tomographic image by X rays of the circuit board 30 being the inspection object is obtained, and position and sort of a defect can be securely grasped even in multi-layer structure.

As above described, according to the present invention, effect an that a clear X-ray tomographic image can be obtained regarding an arbitrary section of an inspection object, and from the clear X-ray tomographic image, a defect in complicated structure of the inspection object can be detected with high reliability.

Also according to the present invention, since a defect in complicated internal structure of the inspection object can be detected with high reliability, effect is in that inspection of a circuit connection portion such as a soldering portion of a multi-layer substrate can be carried out automatically with high reliability.

What is claimed is:

1. An X-ray tomography apparatus comprising:
an X-ray source for irradiating X-rays to an inspection object;
inspection object rotating arrangement for rotating the inspection object in a predetermined direction about a first rotational axis slanted with respect an optical axis of the X-rays irradiated from the X-ray source, said inspection object having a focal plane perpendicular to the first rotational axis and passing through an intersection of the optical axis and the first rotational axis;

still X-ray detecting arrangement for detecting in a state of superposition of a plurality of focal plane X-ray images on the focal plane and of a plurality of nonfocal plane X-ray images outside of the focal plane sequentially transmitted through the inspection object which is rotated in the predetermined direction about the first rotational axis by the inspection object rotating arrangement and for converting the X-ray images into a plurality of optical images;

a collimator lens for collimating the optical rays of the optical images outputted from said still X-ray detecting means to substantially parallel rays;

an optical image rotating prism for rotating the optical images by refracting the parallel rays in synchronization with the rotated inspection object in direction reversed with respect to the predetermined direction about a second rotational axis in parallel to the first rotational axis so as to remove the plurality of nonfocal plane X-ray images by superposition in a state of moving the plurality of nonfocal plane X-ray images against the optical axis of X-rays;

a focusing optical lens for focusing the optical images outputted from the still X-ray detecting arrangement; and photoelectric converting arrangement for receiving the optical images rotated by said optical image rotating prism and focused by said focusing optical lens so as to be superposed and for outputting a clear image signal corresponding to the focal plane X-ray image on an X-ray tomographic image so that the focal plane X-ray image on the X-ray tomographic image is obtained as the clear image signal having the plurality of nonfocal plane X-ray images from the photo-electric converting arrangement removed.

2. The X-ray tomography apparatus as set forth in claim 1, wherein the photoelectric converting arrangement comprises a solid image pickup element.

3. The X-ray tomography apparatus as set forth in claim 1, wherein the still X-ray detecting arrangement includes an X-ray image intensifier.

4. The X-ray tomography apparatus as set forth in claim 1, wherein the still X-ray detecting arrangement includes a fluorescent screen for converting an X-ray image into an optical image, and an image intensifier for amplifying the optical image converted by the fluorescent screen.

5. The X-ray tomography apparatus as set forth in claim 1, wherein the still X-ray detecting arrangement includes a still X-ray image intensifier.

6. The X-ray tomography apparatus as set forth in claim 1, wherein the still X-ray detecting arrangement includes a still fluorescent screen.

7. The X-ray tomography apparatus as set forth in claim 1, wherein the inspection object rotating arrangement comprises:

a Z stage for moving the inspection object in the direction of the first rotational axis; and an X-Y stage for moving the inspection object in the perpendicular direction of the first rotational axis.

8. The X-ray tomography apparatus as set forth in claim 1, wherein said X-ray source is formed by an X-ray tube of a closed type.

9. The X-ray tomography apparatus as set forth in claim 1, wherein the X-ray source comprises:

an electron ray source for converging and irradiating electron rays; and a transmission type target for radiating X-rays by the convergence electron rays irradiated from the electron ray source.

10. The X-ray tomography apparatus as set forth in claim 9, wherein the transmission type target is formed by an X-ray generating layer for generating X-rays, and a support layer for supporting the X-ray generating layer.

11. An X-ray tomography method comprising the steps of:

irradiating X-rays from an X-ray source to an inspection object;

rotating the inspection object in a predetermined direction about a first rotational axis slanted with respect an optical axis of X-rays irradiated from the X-ray source by an inspection object rotation arrangement, the inspection object having a focal plane perpendicular to the first rotational axis and passing through an intersection of the optical axis and the first rotational axis;

detecting, in a state of superposition of a plurality of focal plane X-ray images on the focal plane and of a plurality of nonfocal plane X-ray images outside of the focal plane sequentially transmitted through the inspection object which is rotated in the predetermined direction about the first rotational axis by the inspection object rotating arrangement, by still X-ray detecting arrangement, and converting the X-ray images into a plurality of optical images;

collimating optical rays of the optical images outputted from the still X-ray detecting arrangement to substantially parallel rays by a collimator lens;

rotating the optical images by refracting the parallel rays by an optical image rotating prism in synchronization with the rotated inspection object in a direction reversed to the predetermined direction about a second rotational axis in parallel to the first rotational axis so as to remove the plurality of nonfocal plane X-ray images by superposition in a state of moving the plurality of nonfocal plane X-ray images against the optical axis of X-rays;

focusing the optical images outputted from the still X-ray detecting arrangement by a focusing optical lens; and receiving the optical images rotated by the optical image rotating prism and focused by the focusing optical lens so as to be superposed and for outputting a clear image signal corresponding to the focal plane X-ray image on an X-ray tomographic images by photo-electric converting arrangement so that the focal plane X-ray image on the X-ray tomographic image is obtained as the clear image signal having the plurality of nonfocal plane X-ray images from the photoelectric converting arrangement removed.

12. The X-ray tomography method as set forth in claim 11, wherein the inspection object is moved in the direction of the first rotational axis, and an X-ray tomographic image in an arbitrary section can be obtained.

13. The X-ray tomography method as set forth in claim 11, wherein the inspection object is positioned to the first rotational axis based on obtained data.

14. The X-ray tomography method as set forth in claim 11, wherein X-rays from the X-ray source are radiated from a miniaturized point thereof.

* * * * *